United States Patent [19]

Kobayashi et al.

[11] Patent Number: 4,668,626

[45] Date of Patent: May 26, 1987

[54] METHOD FOR THE PREPARATION OF BRANCHED CYCLODEXTRINS

[75] Inventors: Shoichi Kobayashi; Keiji Kainuma, both of Sakura, Japan

[73] Assignee: Director of National Food Research Institute, Ministry of Agriculture, Forestry and Fisheries, Ibaraki, Japan

[21] Appl. No.: 697,774

[22] Filed: Feb. 4, 1985

[30] Foreign Application Priority Data

Oct. 12, 1984 [JP]  Japan ................................ 59-214001

[51] Int. Cl.⁴ ........................ C12P 19/18; C12P 19/22; C12P 19/20; C12P 19/16
[52] U.S. Cl. ........................................ 435/95; 435/96; 435/98; 435/97
[58] Field of Search ........................ 435/95, 96, 97, 98

[56] References Cited

U.S. PATENT DOCUMENTS 4,384,898  5/1983  Okada et al. .......................... 435/98

OTHER PUBLICATIONS

Chemical Abstracts, vol. 98, 3491v.

Nature, vol. 210, p. 200 (Apr. 9, 1966).

Primary Examiner—Lionel M. Shapiro
Attorney, Agent, or Firm—Frishauf, Holtz, Goodman & Woodward

[57] ABSTRACT

The invention provides an efficient enzymatic method for the preparation of branched cyclodextrins such as glucosyl and maltosyl cyclodextrins. The inventive method comprises the enzymatic reaction of a branch-splitting enzyme and β-amylase simultaneously with a mixture of a cyclodextrin and starch. Alternatively, a branched cyclodextrin is obtained from a mixture of a cyclodextrin and maltose in an enzymatic reaction with pullulanase, optionally, with admixture of an alcohol such as ethyl and propyl alcohols or a glycol such as ethyleneglycol and propyleneglycol to the reaction mixture. A glucosyl cyclodextrin can be obtained by the steps of first subjecting a mixture of a cyclodextrin and maltose to an enzymatic reaction with pullulanase and then subjecting the reaction product to a second enzymatic reaction in the presence of an enzyme mixture composed of takaamylase and glucoamylase and yeast.

17 Claims, 1 Drawing Figure

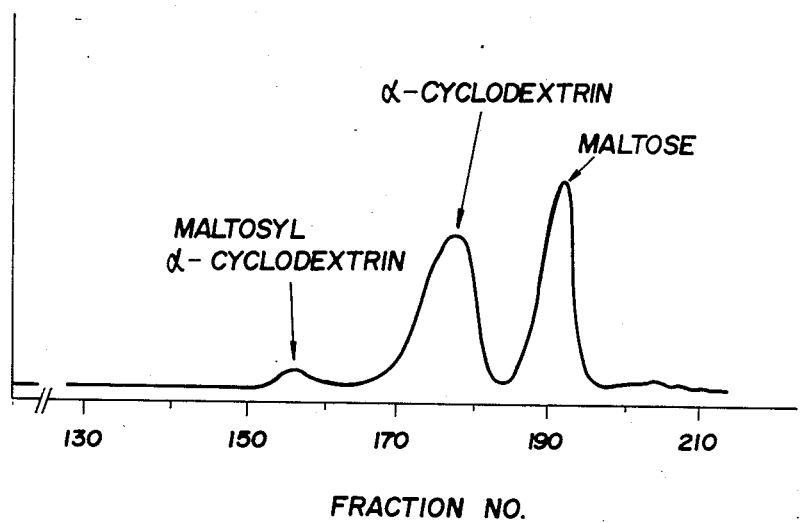

METHOD FOR THE PREPARATION OF BRANCHED CYCLODEXTRINS

BACKGROUND OF THE INVENTION

The present invention relates to a method for the preparation of branched cyclodextrins.

Cyclodextrin is an oligosaccharide formed of at least six glucose units bonded together through α-1,4-linkages and principal known cyclodextrin compounds include α-, β- and γ-cyclodextrins formed of 6, 7 and 8 glucose units, respectively.

Molecules of cyclodextrins have a cavity inherently due to the chemical structure thereof and the cavity exhibits hydrophobicity so that various kinds of oil substances can be incorporated into the cavity and retained therein. By virtue of this unique property, cyclodextrins have found very wide applications and are highlighted in a variety of industries for the manufacture of, for example, medicines, cosmetics and toiletries, perfumes, foodstuffs and the like.

Cyclodextrins generally have low solubility and the values are only about 14, 2 and 23 for the α-, β- and γ-cyclodextrins. β-Cyclodextrin has a particularly low solubility and this is an undesirable and disadvantageous property when practical applications of cyclodextrins are intended.

The inventors have recently conducted extensive investigations on branched cyclodextrins to elucidate the properties thereof [see, for example, Kobayashi, et al. Starch Science, volume 30, pages 231–239 (1983)]. Reportedly, for example, the solubility of the branched cyclodextrin is 10 times larger than that of the corresponding cyclodextrin.

Accordingly, a method has been developed for the preparation of branched cyclodextrins from starch and various types of branched cyclodextrins are being produced by this method. The principle of this method is to roll in the branched parts of the starch molecules to effect the cyclization reaction so that this method is advantageous in that a variety of the branched cyclodextrins are obtained by the method. This method, however, is disadvantageous when a single kind of the branched cyclodextrin is desired.

An attempt has already been made [M. Abdullah and D. French, Nature, volume 210, No. 5052, page 200 (1966)] for the preparation of various kinds of branched cyclodextrins utilizing the reverse action of pullulanase on a mixture of a cyclodextrin and an oligosaccharide. Their works, however, are limited, insofar as in the report, to a mere observation of the reverse action of pullulanase in the paper chromatography and details have not yet been disclosed.

SUMMARY OF THE INVENTION

An object of the present invention is therefore to provide a novel and efficient method for the preparation of branched cyclodextrins free from the above described problems and disadvantages in the prior art methods.

Another object of the present invention is to provide a method for the preparation of branched cyclodextrins utilizing the reverse action of pullulanase and the like branch-splitting enzymes.

According to the disclosure given below, the method of the present invention can be practiced in several different ways. Firstly, branched cyclodextrins are produced by the synergistic enzymatic effect of a branch-splitting enzyme and β-amylase with a mixture of a cyclodextrin and starch. Secondly, branched cyclodextrins are produced by the enzymatic effect of pullulanase with a mixture of a cyclodextrin and maltose. Thirdly, branched cyclodextrins are produced by the enzymatic effect of pullulanase with a mixture of a cyclodextrin and maltose admixed with an alcohol selected from the group consisting of ethyl, n-propyl and isopropyl alcohols or a glycol compound selected from the group consisting of ethyleneglycol and propyleneglycol. Fourthly, the branched cyclodextrins produced by the enzymatic effect of pullulanase with a mixture of a cyclodextrin and maltose are subjected to column chromatographic separation into the individual branched cyclodextrins. Fifthly, glucosyl cyclodextrins are produced by the combined effect of yeast and an enzyme mixture composed of takaamylase and glucoamylase with the reaction product obtained by the enzymatic effect of pullulanase on a mixture of a cyclodextrin and maltose. The cyclodextrin used in the above described various ways for practicing the inventive method is not limited to a cyclodextrin of a particular type among the known cyclodextrins and any of them or a mixture thereof can be used.

BRIEF DESCRIPTION OF THE DRAWING

The FIGURE is a chromatogram for the eluate fractions obtained by the elution with a 10% aqueous solution of ethyl alcohol.

DETAILED DESCRIPTION OF THE PREFERRED EMBODIMENTS

In the first of the above described embodiments of the inventive method, one of the starting materials is starch which is not particularly limitative in respect of the source plant and starch obtained from any starch-producing plant can be used including potatoes, sweet potatoes, corns, glutinous corns, barleys, wheats, cassavas and the like. Starches are composed, for example, of amylose and amylopectin as the compositional fractions. Further, as the decomposition products of starches are named, for example, roasted dextrins such as white dextrin, yellow dextrin, British gum and the like; processed starches such as low-viscosity starches modified by treatment with an enzyme or acid or high-speed mechanical agitation; derivatives of starch such as starch ethers and starch esters including, typically, starch phosphate, starch acetate and the like; physically-treated starches such as those subjected to an irradiation treatment with ionizing radiations or neutron beams, high-frequency treatment or wet-heat treatment; α-starches and the like. These starches and derivatives thereof can be used either singly or as a mixture of two kinds or more.

The mixing ratio of the starch and the cyclodextrin is not particularly limitative but usually 100 parts by weight of the cyclodextrin are mixed with from 50 to 100 parts by weight of the starch material.

The branch-splitting enzyme is preferably pullulanase although isoamylase can also be used. The isoamylase is used advantageously in the preparation of branched cyclodextrins having a branch formed of a compound composed of three or more of the glucose units, e.g. maltotriose, bonded thereto such as a maltotriosyl group. In addition to the conventional pullulanase, the pullulanase used here may be a heat-resistant or acid-resistant pullulanase. The use of a heat-resistant enzyme is advantageous because the solubility of the substrate material can be increased by the increaase of the temperature so that the reverse reaction is accelerated.

The origin of the β-amylase used here is also not particularly limitative including various kinds of plants and microorganisms. Not only highly purified products but also crude products of these enzymes can be used. A continuous process can be designed by use of an enzymatic bioreactor with an immobilized enzyme.

In the first embodiment of the inventive method, the starting material is a mixture of a cyclodextrin and starch so that the combined use of a branch-splitting enzyme and β-amylase is essential in order to hydrolyze the starch into maltose units. In the second to fifth embodiments of the inventive method, on the other hand, the starch in the first embodiment is replaced with maltose so that the β-amylase is no longer required. Incidentally, the pullulanase also pertains to the splitting of the branches in the starch.

In the third embodiment of the inventive method, an alcoholic compound or a glycolic compound is added to the reaction mixture and the addition of these compounds is effective to further improve the efficiency of the reverse reaction by the branch-splitting enzyme so that the yield of the branched cyclodextrins can be increased. The amount of addition of the alcoholic or glycolic compound in this case should be such that the concentration of the added compound in the reaction mixture is in the range from 10 to 40% by weight or, preferably, from 25 to 30%. When the amount of addition is too small, the desired effect mentioned above cannot be fully exhibited while an excessively large amount of the compound gives no additional improvement corresponding thereto sometimes with rather decreased yield of the branched cyclodextrins in comparison with the yield in the case of the absence of these compounds. An additional advantage obtained by the addition of an alcoholic or glycolic compound to the reaction mixture is that the enzymatic reaction can be performed with an increased concentration of each of the cyclodextrin and maltose as the substrates up to about 10 to 15% by weight.

In the fourth embodiment of the invention, the reaction product obtained in the above described second embodiment is subjected to a column chromatography and the maltosyl cyclodextrin as a branched cyclodextrin is isolated therefrom.

Further in the fifth embodiment of the invention, the same reaction product as above is used for the preparation of a glucosyl cyclodextrin by the aid of yeast and an enzyme mixture composed of takaamylase and glucoamylase.

The reverse reaction in the above described inventive method with the branch-splitting enzyme is performed usually with the pH value of the reaction mixture at 4.5 to 6.0 and at a temperature in the range from 30° to 50° C. and the reaction is continued for 24 to 72 hours.

The branched cyclodextrin product obtained by the above described inventive methods is mainly composed of maltosyl cyclodextrins. The first embodiment of the invention is advantageous in the possibility of direct use of starch while the advantage of the second embodiment of the invention is obtained in the improved efficiency for the preparation of the branched cyclodextrins by virtue of the use of maltose as the substrate. Further, the third embodiment of the invention gives an advantage that the reaction proceeds more efficiently than in the second embodiment so that the yield of the branched cyclodextrins is increased.

When a glucosyl cyclodextrin is desired as the branched cyclodextrin product, the reaction product obtained by the above described method is subjected to the reaction by the aid of an enzyme mixture composed of takaamylase and glucoamylase as combined with yeast. Suitable species of the yeast used here are yeasts belonging to the Genus Saccharomyces which include *Saccharomyces cerevisiae Saccharomyces diastaticus* and the like. They are effective to remove the glucose and maltose contained in the reaction mixture by fermentation without decomposing the cyclodextrins and branched cyclodextrins.

In addition to the above described method, the branched cyclodextrin product such as the maltosyl cyclodextrin and the like can be isolated from the reaction mixture by merely standing the reaction mixture at a relatively low temperature of 2° to 10° C. for 20 to 100 hours or, preferably, for 24 to 72 hours. As an alternative method, the reaction mixture is admixed with a precipitant such as trichloroethylene, tetrachloroethane, bromobenzene and the like and shaken for 10 to 20 hours at a temperature of 5° to 10° C. followed by a solid-liquid separation procedure such as centrifugal separation to give the desired branched cyclodextrins. These methods of separation are applicable to the isolation of the branched cyclodextrins other than the maltosyl or glucosyl cyclodextrins from a mixture thereof with other saccharides. Further, these methods can of course be combined with other methods of separation such as a method using an activated carbon adsorbent or ion exchange resin, a method with Sephadex and the like utilizing the difference in the molecular weights, a method using a membrane and the like.

The form of the branched cyclodextrin product obtained by the inventive method can of course be a pure material after further purification but the reaction mixture after the above described back synthesis reaction as such can be the final product depending upon the intended application. These branched cyclodextrins are useful in a wide variety of applications such as solubilization of medicines, cosmetics, perfumes, foods and the like.

In the following, the method of the present invention is described in more detail by way of Testing and Preparatory Examples.

TESTING EXAMPLE 1

Reaction mixtures were prepared each by admixing γ-cyclodextrin with one of the six oligosaccharides ranging from $G_1$, i.e. glucose, to $G_6$, i.e. maltohexaose, in a concentration of 20% by weight to give an overall saccharide concentration of 40% by weight and the mixture was admixed with a commercially available crude enzyme product of pullulanase in an amount of 200 I.U. per g of the overall amount of the substrates to be kept at 40° C. for 48 hours with the pH adjusted to 5.5. The yield of the thus formed branched γ-cyclodextrin is shown in Table 1 for each of the oligosaccharides in a weight percentage based on the overall amount of the starting substrates.

TABLE 1

| $G_1$ | $G_2$ | $G_3$ | $G_4$ | $G_5$ | $G_6$ |
|---|---|---|---|---|---|
| 0 | 12.5 | 8.8 | 6.2 | 4.1 | 3.8 |

The analysis of the branched cyclodextrins was performed by means of the high-performance liquid chromatography (HPLC) and paper chromatography. The conditions for the HPLC were as follows: instrument Tri Rotor by Nippon Bunko Co.; elution with 60 and 65% acetonitrile; flow rate 2 ml/minute; detection by RI; attenuation 8X; column combination of a precolumn of 4.6 mm diameter and 5 cm length and a main column of 4.6 mm diameter and 25 cm length; and stationary phase in the columns Fine sil-NH$_2$ of 10 μm particle diameter. The retention time in minutes for each of the saccharide compounds was as tabulated below, in which the notations of G$_1$-α-CD, G$_2$-α-CD, etc. have the meanings of glucosyl α-cyclodextrin, maltosyl α-cyclodextrin, etc., respectively. CD is an abbreviation for cyclodextrin.

TABLE 2

| | | | |
|---|---|---|---|
| G$_1$ | 4.5 | G$_2$-α-CD | 16.2 |
| G$_2$ | 5.2 | G$_1$-β-CD | 17.1 |
| α-CD | 8.1 | G$_2$-β-CD | 21.4 |
| β-CD | 11.0 | G$_1$-γ-CD | 24.9 |
| G$_1$-α-CD | 12.8 | G$_2$-γ-CD | 28.6 |
| γ-CD | 14.3 | | |

The analysis of the branched cyclodextrins having a branch of G$_2$ or larger by the HPLC and paper chromatography was preceded by the column chromatographic purification using a 2.6×100 cm column filled with Toyopearl HW-40 Super Fine. Further, a similar analysis was undertaken by use of pullulanase with the substrate concentration adjusted to 1% or smaller. The product saccharide by the reverse reaction with pullulanase is a branched cyclodextrin having a single branch per molecule.

TESTING EXAMPLE 2

The same experimental procedure as in Testing Example 1 was repeated with a mixture of γ-cyclodextrin and maltose in equal amounts except that the total sugar concentration was varied in a wide range. The yield of the maltosyl γ-cyclodextrin in % for each total sugar concentration is shown in Table 3 below, in which the saccharide concentration in % is given for each of the substrate saccharides. For example, the concentration of 1% given in the table means that the reaction mixture contained 1% by weight of γ-cyclodextrin and 1% by weight of maltose to give an total sugar concentration of 2% by weight.

TABLE 3

| Saccharide concentration, % | 1 | 2 | 5 | 10 | 15 | 20 | 40 |
|---|---|---|---|---|---|---|---|
| Yield, % | 0.2 | 0.8 | 2.6 | 8.2 | 11.6 | 12.5 | 26.3 |

PREPARATORY EXAMPLE 1

Reaction mixtures were prepared by mixing 100 mg of α-, β- or γ-cyclodextrin and 0.5 ml of each of a 20% solution of liquefied potato starch colored blue with iodine with further admixture of 80 mg of a crude enzyme product of pullulanase having an activity of 2 I.U./mg and 0.5 ml of the supernatant liquid obtained by the centrifugal separation of a solution of 10 mg of a crude enzyme product of soybean β-amylase having an activity of 20 I.U./mg in 1 ml of a 0.1M acetate buffer solution at a pH of 5.5 and the enzymatic reaction was performed with each of the thus prepared reaction mixture at 40° C. for 48 hours with stirring.

The results were that the yields of the branched cyclodextrins were 5.2%, 1.3% and 6.8% for α-, β- and γ-cyclodextrins as the substrate, respectively. It was noted that dissolution of the β-cyclodextrin was incomplete under the above described conditions and a considerable portion thereof remained in the reaction mixture in a crystalline form.

PREPARATORY EXAMPLE 2

Reaction mixtures were prepared by mixing 200 mg of α- or β-cyclodextrin and 200 mg of each of maltose with further admixture of 0.5 ml of the supernatant liquid obtained by the centrifugal separation of a solution of 80 mg of a crude enzyme product of pullulanase having an activity of 2 I.U./mg in 1 ml of a 0.1M acetate buffer solution having a pH of 5.5 together with 0.5 ml of pure water and the enzymatic reaction was performed with each of the thus prepared reaction mixtures at 40° C. for 48 hours with stirring to give a reaction product containing the maltosyl α-cyclodextrin (G$_2$-α-CD) or maltosyl β-cyclodextrin (G$_2$-β-CD) and the unreacted saccharides as the substrates.

Each of the thus obtained reaction mixtures was divided into two equal portions, of which one was kept standing as such for 48 hours at 4° C. and the other was admixed with 200 μl of tetrachloroethane or bromobenzene for the mixture from the α-cyclodextrin or from the β-cyclodextrin, respectively, and shaken overnight at 10° C. followed by centrifugal separation at 5000 r.p.m. for 20 minutes to give a supernatant liquid to be subjected to the determination of the maltosyl cyclodextrin therein. The results are shown in Table 4 in which the content of the maltosyl cyclodextrin in the supernatant liquid is given in % by moles based on the overall content of the cyclodextrin in moles including the values obtained by the analysis of the reaction mixture as such, after the low-temperature standing and after the precipitant treatment.

TABLE 4

| Type of substrate cyclodextrin | Reaction mixture as such | After low-temperature standing | After precipitant treatment |
|---|---|---|---|
| α | 7.0 | 24.9 | 45.3 |
| β | 1.6 | 38.6 | 64.2 |

PREPARATORY EXAMPLE 3

A 2.6×100 cm chromatographic column filled with Toyopearl HW-40 Super Fine was loaded with 1 ml of the reaction mixture obtained in the reaction of Preparatory Example 2 with the α-cyclodextrin as the starting substrate and elution was performed with 10% ethyl alcohol as the eluant at a flow rate of 22 ml/hour to give fractions each having a volume of 2.2 ml. The figure of the accompanying drawing illustrates a chromatogram obtained in this manner showing three definitely splitted peaks corresponding to the respective constituents as indicated.

PREPARATORY EXAMPLE 4

A mixture composed of 1.5 g of α-cyclodextrin and 1.5 g of maltose was admixed with 400 I.U. of a heat-resistant, acid-resistant pullulanase dissolved in 750 μl of a buffer solution having a pH of 4.5 to 5.5 and further with 250 μl of ethyl alcohol and the enzymatic reaction in this reaction mixture was performed at 70° C. for 48 hours to give a yield of the maltosyl α-cyclodextrin as high as 42%.

PREPARATORY EXAMPLE 5

A mixture composed of 300 mg of β-cyclodextrin and 300 mg of maltose was admixed with 750 μl of the same enzyme solution as used in the preceding example and 250 μl of ethyl alcohol and the enzymatic reaction was performed in this reaction mixture at 70° C. for 48 hours to give a yield of the maltosyl β-cyclodextrin of 21%. Further experimentation established that the optimum concentration of ethyl alcohol in the reaction mixture was in the range from 25 to 30% and the yield of the desired product with a concentration of 45% or larger was even lower than the yield without addition of ethyl alcohol.

PREPARATORY EXAMPLE 6

The reaction mixture prepared in the preceding example was subjected to thermal deactivation and 1 ml portion of the mixture was, after adjustment of the pH to 4 to 5, admixed with water to have a total sugar concentration of 20% by weight followed by further addition of 2 mg of glucoamylase, 1 mg of takaamylase and 50 mg of wet fungus body of yeast (*Saccharomyces cerevisiae*). After the enzymatic reaction in this mixture at 30° C. for 48 hours, the reaction mixture was subjected to centrifugal separation and the supernatant liquid was concentrated to give glucosyl β-cyclodextrin. The purity of this product was 78% and the recovery was 65% based on the maltosyl β-cyclodextrin produced in the reaction mixture.

The glucosyl β-cyclodextrin also could be prepared from the reaction mixture obtained in the preceding example by passing the mixture through a column of immobilized enzymes including glucoamylase, takaamylase and yeast.

What is claimed is:

1. A method for the preparation of a maltosyl cyclodextrin which comprises simultaneously reacting a branch-splitting enzyme and β-amylase with a mixture consisting essentially of a cyclodextrin and starch.

2. The method as claimed in claim 1, wherein the cyclodextrin is α-cyclodextrin, β-cyclodextrin, γ-cyclodextrin or a mixture thereof.

3. The method as claimed in claim 1, wherein the branch-splitting enzyme is pullulanase or isoamylase.

4. A method for the preparation of a maltosyl cyclodextrin which comprises reacting pullulanase with a mixture consisting essentially of a cyclodextrin and maltose.

5. The method as claimed in claim 4, wherein the cyclodextrin is α-cyclodextrin, β-cyclodextrin, γ-cyclodextrin or a mixture thereof.

6. A method for the preparation of a maltosyl cyclodextrin which comprises reacting pullulanase with a mixture consisting essentially composed of a cyclodextrin and maltose admixed with an alcoholic compound selected from the group consisting of ethyl alcohol, n-propyl alcohol and isopropyl alcohol or a glycolic compound selected from the group consisting of ethyleneglycol and propyleneglycol.

7. The method as claimed in claim 6, wherein the cyclodextrin is α-cyclodextrin, β-cyclodextrin, γ-cyclodextrin or a mixture thereof.

8. A method for the preparation of maltosyl cyclodextrin which comprises the steps of (a) reacting pullulanase with a mixture consisting essentially of a cyclodextrin and maltose to form the maltosyl cyclodextrin and (b) subjecting the reaction mixture containing the maltosyl cyclodextrin formed in the step (a) to column chromatographic separation to isolate the maltosyl cyclodextrin.

9. The method as claimed in claim 8, wherein the cyclodextrin is α-cyclodextrin, β-cyclodextrin, γ-cyclodextrin or a mixture thereof.

10. A method for the preparation of a glucosyl cyclodextrin which comprises the steps of (a) reacting pullulanase with a mixture consisting essentially of a cyclodextrin and maltose and (b) reacting an enzyme mixture consisting essentially of takaamylase and glucoamylase and yeast with the reaction product obtained in the step (a).

11. The method as claimed in claim 10, wherein the cyclodextrin is α-cyclodextrin, β-cyclodextrin, γ-cyclodextrin or a mixture thereof.

12. The method as claimed in claim 10, wherein the yeast is yeast belonging to the Genus Saccharomyces.

13. The method as claimed in claim 1, wherein the cyclodextrin is α-cyclodextrin, β-cyclodextrin, γ-cyclodextrin or a mixture thereof; the branch-splitting enzyme is pullulanase or isoamylase; and the reaction mixture has a pH of from 4.5 to 6.0.

14. The method as claimed in claim 4, wherein the cyclodextrin is α-cyclodextrin, β-cyclodextrin, γ-cyclodextrin or a mixture thereof; and the reaction mixture has a pH of from 4.5 to 6.0.

15. The method as claimed in claim 6, wherein the cyclodextrin is α-cyclodextrin, β-cyclodextrin, γ-cyclodextrin or a mixture thereof; and the reaction mixture has a pH from 4.5 to 6.0.

16. The method as claimed in claim 8, wherein the cyclodextrin is α-cyclodextrin, β-cyclodextrin, γ-cyclodextrin or a mixture thereof; and the reaction mixture has a pH of from 4.5 to 6.0.

17. The method as claimed in claim 10, wherein the cyclodextrin is α-cyclodextrin, β-cyclodextrin, γ-cyclodextrin or a mixture thereof; the yeast is yeast belonging to the Genus Saccharomyces; and the pH of the reaction mixture of step (a) is from 4.5 to 6.0.

* * * * *

UNITED STATES PATENT AND TRADEMARK OFFICE
CERTIFICATE OF CORRECTION

PATENT NO. : 4,668,626

DATED : MAY 26, 1987

INVENTOR(S) : KOBAYASHI et al

It is certified that error appears in the above-identified patent and that said Letters Patent is hereby corrected as shown below:

Column 8, line 3 (Claim 6): delete "composed".

Signed and Sealed this

Twenty-ninth Day of March, 1988

Attest:

DONALD J. QUIGG

Attesting Officer

Commissioner of Patents and Trademarks